United States Patent [19]
Lipinski

[11] 3,941,889

[45] Mar. 2, 1976

[54] 5-(SUBSTITUTED PHENOXY)-4-AMINO PYRIMIDINES AS ANTI-ULCER AGENTS

[75] Inventor: Christopher Andrew Lipinski, Waterford, Conn.

[73] Assignee: Pfizer Inc., New York, N.Y.

[22] Filed: Nov. 4, 1974

[21] Appl. No.: 520,486

Related U.S. Application Data

[62] Division of Ser. No. 287,423, Sept. 8, 1972, Pat. No. 3,862,190.

[52] U.S. Cl. .................................................. 424/251
[51] Int. Cl.² ......................................... A61K 31/505
[58] Field of Search ..................................... 424/251

[56] References Cited
UNITED STATES PATENTS 3,862,190    1/1975    Lipinski .............................. 424/251

OTHER PUBLICATIONS

Chemical Abstracts, Vol. 55 (1961), p. 25973c.

*Primary Examiner*—V. D. Turner
*Attorney, Agent, or Firm*—Connolly and Hutz

[57]  ABSTRACT

The preparation of novel 5-(substituted phenoxy)-4-amino and substituted amino pyrimidines is described. These compounds, possessing anti-secretory and anti-ulcer activity, are effective anti-ulcer agents.

1 Claim, No Drawings

5-(SUBSTITUTED PHENOXY)-4-AMINO PYRIMIDINES AS ANTI-ULCER AGENTS

CROSS REFERENCE TO RELATED APPLICATION

This application is a divisional application Ser. No. 287,423 filed Sept. 8, 1972, now U.S. Pat. No. 3,862,190.

BACKGROUND OF THE INVENTION

This invention relates to new 5-(substituted phenoxy)-4-amino and substituted amino pyrimidines and to their use as anti-ulcer agents.

Chronic gastric and duodenal ulcers, collectively known as peptic ulcers, are a common affliction for which a variety of treatments have been developed. The treatment depends upon the severity of the ulcer and may range from dietary and drug treatment to surgery. The administration of atropine and other anticholinergic drugs to combat gastric hyperacidity is a common treatment for peptic ulcers. Treatment with such agents produces undesirable side effects such as tachycardia, mydriasis, dry skin and mouth and diarrhea.

An effective treatment for peptic ulcers is desirable in which a gastric anti-secretory effect is achieved by a non-anticholinergic mechanism thus avoiding the undesirable side effects of anticholinergic agents.

SUMMARY OF THE INVENTION

It has been found that 5-(substituted phenoxy)-4-amino and substituted amino pyrimidines of the formulae below are effective inhibitors of gastric acid secretion and are affective anti-ulcer agents:

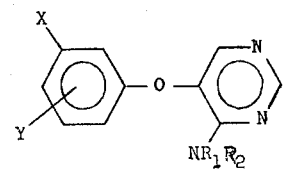

wherein X and Y are each hydrogen, chlorine, bromine, fluorine, alkyl containing from 1 to 6 carbon atoms, trifluoromethyl or alkoxy containing from 1 to 3 carbon atoms in the alkyl moiety;

$R_1$ and $R_2$ are each hydrogen or alkyl containing from 1 to 6 carbon atoms.

Also included in this invention are the pharmaceutically-acceptable acid addition salts as represented by the hydrochloride, hydrobromide, sulfate, phosphate, nitrate, acetate, propionate, butyrate, citrate, gluconate, malate, tartrate, benzoate, succinate, maleate and fumarate.

DETAILED DESCRIPTION OF THE INVENTION

The compounds of this invention are related chemically to substituted pyrimidines reported in J. Org. Chem. 75, 438 (1970), J. Org. Chem. 26, 2770 (1961), J. Am. Chem. Soc. 73, 3753 (1951) and Chemical Abstracts 49, 7606b.

Representative of the compounds of this invention is the preparation of 4-amino-5-phenoxy pyrimidine hydrochloride as shown in the following synthetic routes.

Route A

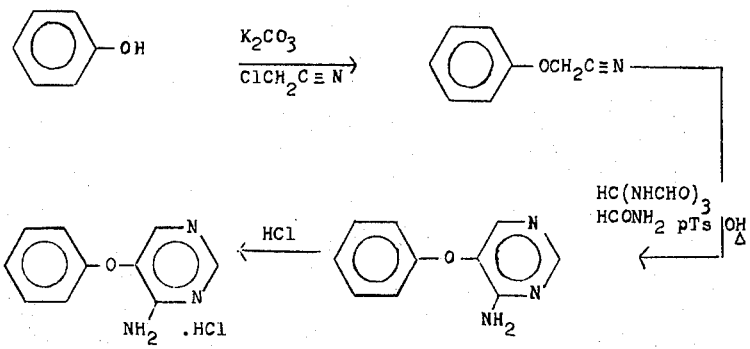

Route B

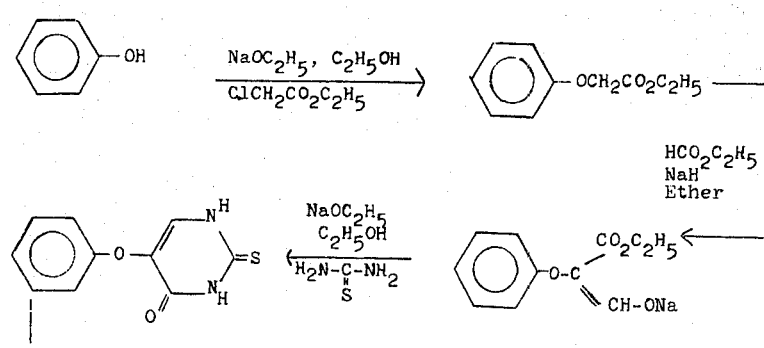

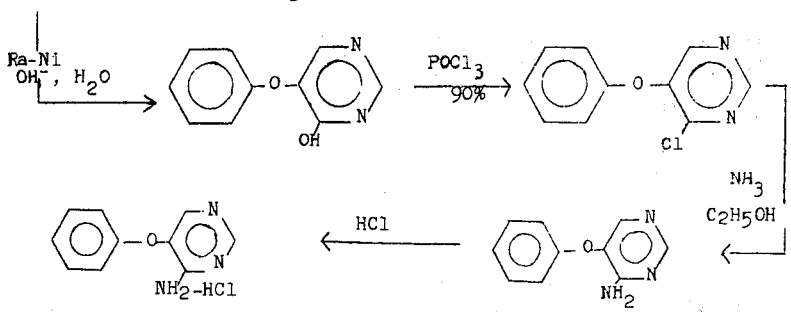

Method B is the preferable synthetic route with a somewhat greater overall yield than Method A.

Phenoxy ethyl acetate is prepared by the procedure of J. Munch-Peterson, Acta Chem. Scand. 5, 519 (1951).

The sodium salt of ethyl α-phenoxy-β-hydroxyacrylate is prepared by a procedure adapted from that of T.B. Johnson and H.H. Guest, Am. Chem. J. 42, 271 (1909). Similarly, the synthesis of 2-thio-4-hydroxy-5-phenoxy pyrimidine is that reported by T.J. Johnson and H.H. Guest, Am. Chem. J. 42, 286 (1909).

The preparation of 4-hydroxy-5-phenoxy pyrimidine is accomplished by adding wet Raney-Nickel to an alkaline solution of 2-thio-4-hydroxy-5-phenoxy pyrimidine and heating at reflux for about 2 hours. The product is obtained by collecting the solid that precipitates on acidifying the filtered solution. The hydroxy compound is converted to the chloro compound by heating at about 70°C. with phosphorus oxychloride, adding ammonium hydroxide to about pH 8 and extracting several times with chloroform. A colorless oil is obtained on distillation under vacuum.

4-Chloro-5-phenoxy pyrimidine is dissolved in absolute ethanol saturated with ammonia and added ammonium chloride, and heated in a stainless steel pressure bomb at about 160°C. for approximately 6 hours. The ethanol is removed under vacuum, and the oily residue taken up in ether. Concentration of the ether extract gives 4-amino-5-phenoxy pyrimidine as a yellow solid which is taken up in hot ethyl acetate, treated with activated charcoal, filtered and cooled to provide white crystals.

The phenoxy substituted compounds of this invention are prepared in analogous manner starting with appropriately substituted phenols. Substitutions in the pyrimidine moiety are obtained by treating the 4-chloro compound with an appropriate amine.

The compounds described herein are effective antiulcer agents via the intraperitoneal and oral routes of administration against gastric ulcers. These products not only accelerate healing of such ulcers but also prevent formation of ulcers and decrease gastric acid output in animals. They can, therefore, be said to be useful for the control of peptic ulceration.

The valuable products of this invention can be administered alone or in combination with a pharmaceutical carrier selected on the basis of the chosen route of administration and standard pharmaceutical practice. For example, they can be administered orally in the form of tablets containing such excipients as polyvinylpyrrolidone, a Carbowax (non-volatile, solid polyethylene glycols available from Carbide and Carbon Chemicals Corporation), especially Carbowax 6000, starch, milk sugar, etc. or in capsules alone or in admixture with the same or equivalent excipients. They may also be administered orally in the form of elixirs or oral suspensions which may contain flavoring or coloring agents or be injected parenterally; that is, for example, intramuscularly or subcutaneously. For parenteral administration, they are best used in the form of a sterile solution which may be either aqueous such as water, isotonic saline, isotonic dextrose, Ringer's solution, or non-aqueous such as fatty oils of vegetable origin (cotton seed, peanut oil, corn, sesame) and other non-aqueous vehicles which will not interfere with the therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents as well as local anesthetics and inorganic salts to afford desirable pharmacological properties.

For both oral and intraperitoneal administration, a dosage range of from about 150 mg. to about 300 mg. per day is effective. The dosage level can, with careful supervision, range up to as high as about two grams per day. Propylene glycol is a suitable and convenient carrier or diluent for intraperitoneal use. Carbowax 6000 is a favored excipient for oral use. Compositions containing from about 50% to about 90% by weight of polyvinylpyrrolidone or Carbowax 6000 are especially effective for oral administration. Higher or lower amounts of excipient can, of course, be used but appear to offer no advantages over these proportions. For intraperitoneal use, the polyvinylpyrrolidone formulations are suspended in carriers such as water or in saline solution containing 1% carboxymethylcellulose and 0.1% Tween 80 (polyoxyethylene ethers of partial esters of fatty acids and hexitol anhydrides derived from sorbitol, available from Atlas Chemical Industries, Inc.). The water soluble products of this invention are conveniently administered in water solution.

The effectiveness of the products of this invention as antiulcer agents is determined by the stressed rat assay as follows.

Cold-Restraint Stressed Rat: Non-fasted female rats (Charles River C-D strain) weighing 70–140 gms. are administered the drug or carrier (control animals) intraperitoneally (in saline solution containing 1% carboxymethylcellulose and 0.1% Tween 80) or orally (in water) three hours before being lightly anesthetized with ether and taped in the supine position to individual sheets of acrylic plastic (Plexiglass, Rohm & Haas Co.). After recovery from the anesthesia, the restrained animals are positioned horizontally in a refrigerator maintained at 10°–12°C. and three hours later sacrificed by cervical dislocation. The abdomen of each rat is opened, the pylorus clamped, the stomach inflated with saline via an oral tube, the esophagus clamped and the stomach excised. The stomachs are placed in a 0.4% formaldehyde solution for approximately 30 seconds to harden the outer layers and facilitate examination.

Each stomach is then cut open along the greater curvature and the glandular portion (hind stomach) examined for damage. The number of gastric erosions, their severity and the color of the stomachs is recorded. The Mann-Whitney-Wilcoxon rank sum test is used to compare the median number of gastric erosions in the control group with the median number of gastric erosions in each drug-treated group to determine if they are statistically different. (Dixon et al., "Introduction to Statistical Analysis," 3rd Ed., McGraw-Hill Book Company, New York, pp. 344–347, 1969)

Their effect on gastric acid output in pylorus-ligated (i.e. Shay) rats is determined by the following procedure:

Shay Rat: Forty-eight hours before surgery female rats (Charles River C-D strain; 100–140 gms.) are individually caged and taken off normal food. Each animal is given two sugar cubes and water ad libitum to effect emptying of the stomach. Drug or carrier is administered intraperitoneally and three hours later, under ether anesthesia, the abdomen is shaved and opened along the linea alba. After exposing and ligating the pylorus, the incision is closed and the animal is returned to its cage and allowed to regain consciousness. Three hours later the animal is sacrificed by cervical dislocation, the abdomen reopened, the distal esophagus clamped, and the stomach excised. The stomach is cut open and the contents washed into a beaker with one ml. of deionized water. The volume of gastric juice is recorded following centrifugation. Excessively dirty (greater than 0.5 ml. of solids) or bloody samples are discarded. The acidity of one ml. of gastric juice is determined by titration with a standardized NaOH (0.1N) solution using phenolphthalein as an indicator and total acid output ($\mu$eqH$^+$/100 gms. body weight/3 hours) is calculated. A non-paired $t$ test is used to compare the means of the control and tested groups. (Dixon et al., Technometrics, X, 83–98, 1968.)

EXAMPLE I

Preparation of Phenoxy ethyl acetate

To a suspension of 136 g. sodium ethoxide (2.0 mol) in 1500 ml. absolute ethanol was added 188 g. (2.0 mol) phenol followed by dropwise addition of 245 g. (2.0 mol) ethyl chloroacetate. The mixture was heated at reflux for 18 hrs. during which time sodium chloride precipitated from solution. The reaction mixture was cooled to room temperature and filtered from insoluble salts and concentrated in vacuo to an amber oil. The filter cake was washed with ether and the ether was concentrated on a steam bath to an oil. The oils were combined and distilled to give 283 g. (78%) of a colorless oil, b.p. 100°/4mm lit b.p. 250°/760 mm.

Preparation of Sodium Salt of Ethyl α-Phenoxy-β-hydroxyacrylate

To a suspension of 48 g. NaH (57% oil suspension - 1.1 mol) in 500 ml. of anhydrous ether cooled to 8° to 10°C. was added dropwise a solution of 74 g. (1.0 mol) ethyl formate, 180 g. (1.0 mol) phenoxy ethyl acetate and 100 ml. anhydrous ether. During the addition the temperature was maintained at 8° to 10° by cooling in an ice bath. After the addition was completed the solution was allowed to warm to room temperature and was stirred at room temperature for 2.5 hours during which time a thick slurry of the product crystallized out of solution. The suspension was filtered on a Buchner funnel and washed well with 4:1 hexane-ether and oven dried to give 112 g. (49%) of an amorphous white solid suitable for reaction in the next step of the synthetic sequence.

Preparation of 2-Thio-4-Hydroxy-5-phenoxy pyrimidine

To a suspension of 34.0 g. sodium ethoxide (0.5 mol) in 600 ml. of absolute ethanol was added 56.0 g. (0.25 mol) of the sodium salt of ethyl α-phenoxy-β-hydroxyacrylate and 38.0 g. (0.5 mol) of thiourea. The mixture was stirred and heated at reflux for 3 hrs. One third of the volume of ethanol solvent was removed by distillation and the solution was slowly added to an iced acetic acid solution to precipitate a white solid which was collected by vacuum filtration and oven dried to give 44.0 g. (80%) mp 250°–253° lit mp 253–254.

Preparation of 4-hydroxy-5-phenoxypyrimidine

To a solution of 22.0 g. (0.55 mol) of sodium hydroxide in 700 ml. of water was dissolved 121 g. (0.55 mol) of 2-thio-4-hydroxy-5-phenoxy pyrinidine. To the stirred solution was added slowly 1250 g. of wet Raney-Nickel at such a rate that the resultant foaming remained under control. The mixture was stirred well and heated at reflux for 2 hrs. The suspension was filtered while still hot and the Raney-Nickel residue washed with 1.5 l of boiling water with care being taken that the catalyst remained wet. The combined aqueous solutions were concentrated to 700 ml. and acidified with acetic acid to precipitate a white solid. This was collected by filtration and oven dried to give 85.5 g. (82.5%) mp 186°–188°.

Anal. Calcd: C, 63.82; H, 4.28; N, 14.89;
Found: C, 63.62; H, 4.51; N, 14.90

Preparation of 4-chloro-5-phenoxy pyrimidine

To 500 ml. of phosphorus oxychloride was added 85.5 g. (0.455 mol) of 4-hydroxy-5-phenoxy pyrimidine and the suspension heated at 70° in an oil bath. After 1 hr the reaction mixture became homogeneous and after 1.5 hr total reduction time the bulk of the phosphorus oxychloride was removed by distillation at reduced pressure. The residue was slowly added to well stirred iced water and the residual acid was cautiously neutralized with ammonium hydroxide solution to pH 8 and was extracted with 3 × 700 ml. of chloroform. The chloroform extracts were dried over anhydrous sodium sulfate filtered and concentrated in vacuo to 85.7 g. (90%) of a black oil. A colorless oil could be obtained by evaporative distillation of this material at 130° (0.1 mm).

Anal. Calcd: C, 58.12; H, 3.42; N, 13.56; Cl, 17.16;
Found: C, 57.83; H, 3,54; N, 13.71; Cl, 17.25

Preparation of 4-amino-5-phenoxy pyrimidine

To a solution of 125 ml. of absolute ethanol saturated with ammonia was added 2.0 g. ammonium chloride and 25.7 g. (0.124 mol) of 4-chloro-5-phenoxy pyrimidine and the mixture was heated in a 250 ml. stainless steel pressure bomb at 160° for six hrs. The bomb was cooled and the contents poured into a 1000 ml. rb flask. The bomb was rinsed with 4 × 100 ml. boiling ethanol and the combined ethanol solutions were stripped to an oily mixture on the rotary evaporator. The residues were extracted with 4 × 150 ml ether and the ether solution concentrated on the steam bath until a solid began to precipitate. Cooling gave a yellow solid which was collected by vacuum filtration. The solid was taken up in hot ethyl acetate and treated with activated charcoal filtered and concentrated on the steam bath. Careful addition of hexane and cooling gave 15.3 g (66%) white crystals mp 118°–120°.

Anal. Calcd: C, 64.16; H, 4.85; N, 22.45;
Found: C, 64.21; H, 5.02; N, 22.61

Preparation of 4-amino-5-phenoxy pyrimidine hydrochloride

To a solution of 15.3 g. (0.082 mol) of 4-amino-5-phenoxy pyrimidine in 100 ml. of 5% methanol in ethyl acetate was slowly added an ethyl acetate solution saturated with HCl gas. The clear solution was heated on a steam bath to remove the methanol until the solution became slightly cloudy. Cooling gave 10.2 g. (55%) of white crystalline solid mp 220°–221°.

Anal: C, 53.70; H, 4.51; N, 18.78;
Found: C, 53.77; H, 4.57; N, 18.48

Titration in 50% ethanol-50% water gave $pK_a = 4.1$. Infrared spectra shows the hydrochloride salt is ring protonated. The compound is soluble at >20 mg/ml in water.

EXAMPLE II

The procedure described in Example I is employed to prepare the following 5-(substituted phenoxy)-4-amino and substituted amino pyrimidines exmploying appropriate phenols and amines.

| X | Y | R₁ | R₂ |
|---|---|---|---|
| hydrogen | hydrogen | methyl | ethyl |
| hydrogen | 2-chloro | n-butyl | n-propyl |
| 3-chloro | hydrogen | n-hexyl | methyl |
| hydrogen | 2-bromo | hydrogen | hydrogen |
| 3-bromo | hydrogen | ethyl | ethyl |
| hydrogen | 4-bromo | methyl | methyl |
| hydrogen | 4-fluoro | n-amyl | n-amyl |
| 3-chloro | 4-chloro | isopropyl | isopropyl |
| 3-bromo | 5-bromo | hydrogen | hydrogen |
| hydrogen | 2-methyl | hydrogen | hydrogen |
| 3-ethyl | hydrogen | methyl | methyl |
| hydrogen | 4-hexyl | ethyl | ethyl |
| 3-methyl | 2-methyl | n-propyl | n-propyl |
| 3-methyl | 4-chloro | hydrogen | hydrogen |
| 3-bromo | 5-propyl(n) | methyl | ethyl |
| 3-isopropyl | 6-fluoro | hydrogen | hydrogen |
| 3-methoxy | hydrogen | hydrogen | methyl |
| 3-trifluoromethyl | hydrogen | ethyl | hydrogen |
| 3 ethoxy | 4-methyl | hydrogen | hydrogen |

TABLE

Antiulcer Activity in Stressed Rat Assay

| X | Y | Z | Route* | Dose Mg/Kg | % Reduction in Incidence of Damage |
|---|---|---|---|---|---|
| H | H | NH₂.HCl | P.O. | 100 | 50 |
| H | H | NH.CH₃ | I.P. | 100 | 80 |
| H | H | N(CH₃)₂ | I.P. | 100 | 60 |
| H | H | NH₂.HCl | P.O. | 10 | 35 |

TABLE II
Antisecretory Activity

| X | Y | Z | Route* | Dose Mg/Kg | % Inhibition of Acid Secretion |
|---|---|---|---|---|---|
| H | H | NH₂.HCl | I.V. | 25 | 70 |
| Cl | H | NH₂ | I.V. | 25 | 59 |
| H | 2-Cl | NH₂ | I.V. | 25 | 11 |
| F | H | NH₂ | I.V. | 12.5 | 29 |
| CH₃ | H | NH₂ | I.V. | 12.5 | 34 |
| H | H | NH.CH₃ | I.V. | 25 | 80 |
| H | H | N(CH₃)₂ | I.V. | 25 | 60 |

*P.O. - oral
I.P. - intraperitoneal
I.V. - intravenous

What is claimed is:

1. A method for the control of ulcers in an animal which comprises administering orally or intraperitoneally to an animal in need of such control a composition containing a diluent amount of a pharmaceutically-acceptable carrier and an amount effective to control said ulcers of a compound selected from the group consisting of and a pharmaceutically-acceptable acid addition salt thereof, wherein X and Y are each hydrogen, chlorine, bromine, fluorine, alkyl containing from 1 to 6 carbon atoms, trifluoromethyl or alkoxy containing from 1 to 3 carbon atoms in the alkyl moiety; R₁ and R₂ are each hydrogen to alkyl containing from 1 to 6 carbon atoms.

* * * * *